United States Patent [19]

Rauchschwalbe et al.

[11] 4,366,102
[45] Dec. 28, 1982

[54] PROCESS FOR THE PREPARATION OF CHLOROFORMIC ACID ARYL ESTERS

[75] Inventors: Günter Rauchschwalbe, Cologne; Heinz U. Blank, Odenthal; Karl Mannes; Dietmar Mayer, both of Leverkusen, all of Fed. Rep. of Germany

[73] Assignee: Bayer Aktiengesellschaft, Leverkusen, Fed. Rep. of Germany

[21] Appl. No.: 261,082

[22] Filed: May 6, 1981

[30] Foreign Application Priority Data

May 22, 1980 [DE] Fed. Rep. of Germany ....... 3019526

[51] Int. Cl.³ ........................................... C07C 68/02
[52] U.S. Cl. .................................. 260/463; 549/214; 549/479; 549/474; 549/478; 549/454; 542/400; 542/454; 542/468; 546/103; 546/141; 546/147; 546/153; 546/154; 546/157; 546/302; 549/23; 549/66; 549/410; 549/470; 548/406; 548/510
[58] Field of Search ............ 260/463, 326.2, 326.13 B, 260/326.13 A, 326.13 R, 343.44, 345.2, 347.3; 542/454, 468, 450; 546/302, 153, 154, 157, 141, 147, 103; 549/66, 23

[56] References Cited

U.S. PATENT DOCUMENTS

| | | | |
|---|---|---|---|
| 3,170,946 | 2/1965 | Kilsheimer et al. | 260/463 |
| 3,211,774 | 10/1965 | Stephens | 260/463 |
| 3,211,775 | 10/1965 | Stephens et al. | 260/463 |
| 3,211,776 | 10/1965 | Stephens | 260/463 |
| 3,255,230 | 6/1966 | Kurkjy et al. | 260/463 |
| 3,382,207 | 5/1968 | Jaquiss | 260/463 |
| 3,544,626 | 12/1970 | Carr et al. | 260/544 |
| 3,673,247 | 6/1972 | Hill et al. | 260/543 R |
| 3,792,075 | 2/1974 | Kaminaka et al. | 260/463 |
| 3,822,307 | 7/1974 | Fujimoto et al. | 260/463 |
| 3,952,045 | 4/1976 | Gaenzler et al. | 260/463 |
| 3,966,786 | 6/1976 | Rozsa et al. | 260/463 |
| 4,085,129 | 4/1978 | Semter et al. | 260/463 |
| 4,129,595 | 12/1978 | Suzuki | 260/544 Y |

FOREIGN PATENT DOCUMENTS

2325088 12/1974 Fed. Rep. of Germany .
2804227 8/1978 Fed. Rep. of Germany .
1200768 8/1970 United Kingdom .

OTHER PUBLICATIONS

Derwent Japanese Patents Report; vol. 6, No. 13 7890/67 and No. 45 23409/67 (1967).

*Primary Examiner*—Mary C. Lee
*Attorney, Agent, or Firm*—Sprung, Horn, Kramer & Woods

[57] ABSTRACT

In a process for the preparation of an aromatic chloroformic acid ester by contacting a phenol and phosgene, the improvement wherein the reaction is carried out in a homogeneous liquid phase at a temperature of 60° to 180° C. in the presence of organic phosphorus compound of the formula

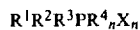

$$R^1R^2R^3PR^4{}_nX_n$$

in which

R¹, R² and R³ independently of one another represent hydrogen, alkyl, alkenyl, aralkyl, aryl or halogen and two of the said radicals together with the phosphorus atom can form a 5-membered or 6-membered phosphorus-containing saturated or unsaturated heterocyclic radical, X represents OH, homopolar-bonded halogen or an inorganic or organic acid anion, R⁴ denotes hydrogen or alkyl or, if X denotes halogen, can also denote halogen and n denotes 0 or 1, and in which, furthermore, R⁴ and X together can represent oxygen or sulfur.

10 Claims, No Drawings

PROCESS FOR THE PREPARATION OF CHLOROFORMIC ACID ARYL ESTERS

The invention relates to a process for the preparation of chloroformic acid aryl esters by reacting phenols with phosgene in the presence of organic phosphorus compounds.

The reaction of alcohols or phenols with phosgene to give the corresponding chloroformic acid esters has already been disclosed (Ullmanns Enzyklopädie der technischen Chemie (Ullmann's Encyclopaedia of Industrial Chemistry), 4th Edition, Volume 9, page 381, Verlag Chemie, 1975). Whilst aliphatic alcohols are able to react with phosgene even without additives, additives, for example those which are able to bind the hydrochloric acid liberated, must be used when reacting phosgene with phenols.

Thus, for example, inorganic bases, such as aqueous sodium hydroxide solution, can be employed (German Auslegeschrift No. 1,117,598 and British No. 1,200,768). These bases must be used in at least the stoichiometric amount and this has an adverse effect on the economy of the process and give rise to disposal problems since at least stoichiometric amounts of inorganic salts are formed. Furthermore, the procedure in the water/organic solvent two-phase system impairs the space-time yield of the process.

The addition of organic nitrogen bases has also been disclosed (German Auslegeschrift No. 1,213,419 and U.S. Pat. No. 3,211,776).

However, the use of these bases makes it necessary to carry out the reaction in an organic solvent or under elevated pressure in an autoclave. This also has an adverse effect on the space-time yield of the process, or necessitates the use of apparatus for working under pressure. The hydrochloride formed from the amine base added and the hydrogen chloride liberated must be removed from the reaction mixture, for example by washing the solution, extracting, filtering or decanting, since otherwise the hydrochloride formed can block the apparatus during the subsequent distillation and results in breakdowns. To avoid these complications, the reaction can be carried out in the presence of a resin which contains amino groups (U.S. Pat. No. 3,211,775), but in this case also the reaction must be carried out under pressure. The additional costs for these polymeric catalysts are a burden on the economy of the process. Furthermore, working with phosgene and the resulting hydrogen chloride under pressure is expensive in respect of corrosion and the maintenance of work safety.

Furthermore, quaternary ammonium salts promote the reaction of phosgene with phenols (U.S. Pat. No. 3,255,230). In this case also it is necessary to carry out the reaction in a solvent. Good yields are obtained with this process using ammonium salts which carry long-chain aliphatic substituents, such as stearyltrimethylammonium chloride (Chem. and Ind. 1965, 791 to 793). These additives are separated off by filtration or chromatography and this, like the special additives, results in higher costs.

Furthermore, carboxylic acid amides, such as dimethylformamide, have also been recommended as catalytically effective additives (German Auslegeschrift No. 2,131,555; U.S. Pat. No. 3,211,774). However, during the preparation of chloroformic acid phenyl ester, dimethylformamide and phosgene form N,N-dimethylcarbamoyl chloride, which has a highly carcinogenic action on mice (C.A. 77, 97 540 b).

The use of trisubstituted phosphines or phosphine oxides for the preparation of hydroxybenzenesulphonic acid halides from the sulphonic acid salts on which the latter are based and thionyl chloride, phosphorus oxychloride or phosgene has been disclosed in U.S. Pat. No. 3,673,247. Furthermore, the use of phosphine chloride compounds and phosphine oxide compounds for the preparation of carboxylic acid chlorides from the carboxylic acids has been disclosed (German Offenlegungsschrift No. 2,841,069, German Offenlegungsschrift No. 2,321,122, U.S. Pat. Nos. 3,544,626 and 4,129,595).

The reaction of phenols with phosgene in the presence of sodium hydroxide solution and in the presence of quaternary phosphorus compounds results in the formation of diaryl carbonates (German Offenlegungsschrift No. 2,804,227 and French No. 1,381,791).

Furthermore, it is known that aliphatic alcohols react with phosgene to form chloroformates if a trialkyl phosphite or PCl₃, which under the reaction conditions forms a trialkyl phosphite, is added (Japanese Applications Nos. 23409/67 and 7890/67). Aliphatic alcohols can, however, also be converted to chloroformates without additives, so that no technical advance is discernible by the additions of phosphite or PCl₃. Phenol, on the other hand, does not react with phosgene in the presence of triethyl phosphite in the temperature ranges of up to 35° C. indicated in the Japanese Patent Applications, whilst at elevated temperature diphenyl carbonate forms.

A process for the preparation of aromatic chloroformic acid esters from phenols and phosgene has now been found which is characterized in that the reaction is carried out in a homogeneous liquid phase at a temperature of 60° to 180° C. in the presence of organic phosphorus compounds of the formula

$$R^1R^2R^3PR^4{}_nX_n \qquad (I)$$

in which
$R^1$, $R^2$ and $R^3$ independently of one another represent hydrogen, alkyl, alkenyl, aralkyl, aryl or halogen and two of the said radicals together with the phosphorus atom can form a 5-membered or 6-membered phosphorus-containing saturated or unsaturated heterocyclic radical, X represents OH, homopolar-bonded halogen or an inorganic or organic acid anion, $R^4$ denotes hydrogen or alkyl or, if X denotes halogen, can also denote halogen and n denotes 0 or 1, and in which, furthermore, $R^4$ and X together can represent oxygen or sulphur.

An example of alkyl which may be mentioned is a straight-chain, branched or cyclic radical with up to 12, preferably 8 and particularly preferentially 6 carbon atoms, such as methyl, ethyl, propyl, isopropyl, butyl, isobutyl, tert.-butyl, pentyl, hexyl, decyl, dodecyl, cyclohexyl or 4-ethyl-cyclohexyl. Preferred alkyl radicals are butyl or cyclohexyl.

Examples of alkenyl which may be mentioned are straight-chain, branched or cyclic radicals with at least one olefinic double bond and 2 to 12, preferably up to 8 and particularly preferentially up to 6 carbon atoms, such as 1-propenyl, 2-propenyl, butenyl, 3-methyl-2- butenyl and hexenyl. Preferred alkenyl is propenyl or butenyl.

Radicals which may be mentioned as aralkyl are hydrocarbon radicals which have an aliphatic and an aromatic part, such as benzyl, phenylethyl, naphthylmethyl, naphthyl-ethyl and 9-fluorenyl, preferably benzyl.

Radicals which may be mentioned as aryl are aromatic hydrocarbon radicals with up to 15, preferably up to 10 and particularly preferentially up to 7 carbon atoms, such as phenyl, tolyl, naphthyl, ethylnaphthyl, anthryl, methylanthryl, fluorenyl or biphenyl, preferably phenyl or tolyl.

Examples of halogen which may be mentioned are chlorine and bromine, preferably chlorine.

If two of the radicals $R^1$ to $R^3$ together with the phosphorus form a 5-membered or 6-membered phosphorus-containing saturated or unsaturated heterocyclic radical, examples of such radicals which may be mentioned are the phosphol system, the phospholene system, the phospholane system, the dibenzophospholane system or the phosphacyclohexane system, preferably the phospholene system or the phospholane system.

In addition to hydroxyl, the substituent X in the formula (I) can also be homopolar-bonded halogen, for example chlorine or bromine. The substituent X can also be the inorganic or organic acid anion of a phosphonium salt, for example chloride, bromide, sulphate, phosphate, methyl-sulphate or aliphatic or aromatic sulphonate.

Furthermore, the radicals $R^4$ and X together can represent oxygen or sulphur, preferably oxygen.

n denotes 0 or the number 1 and specifically in each case has the same meaning for the radical $R^4$ and for X.

The organic phosphorus compounds of the formula (I) include, for example, phosphines, phosphine oxides, phosphine sulphides, phosphine halides, phosphonium salts or halogenophosphines.

Examples of phosphines which may be mentioned are: tributylphosphine, triphenylphosphine, methyldiphenylphosphine, diethylcyclohexylphosphine, tricyclohexylphosphine, allyl-butyl-phenylphosphine, methylbenzyl-tolylphosphine, 1-methylphosphol, 1-methyl-2,5-dihydrophosphol, 1-phenyl-2-methyl-2,5-dihydrophosphol and 1-methyl-dibenzophospholane. Preferred phosphines are tributylphosphine, triphenylphosphine and 1-phenyl-2-methyl-2,5-dihydro-phosphol.

Examples of phosphine oxides which may be mentioned are: 1-methylphosphol oxide, 1-phenyl-2-methyl-2,5-dihydrophosphol oxide, tributylphosphine oxide, triphenylphosphine oxide and triphenylphosphine oxide hydrate, preferably triphenylphosphine oxide.

An example of a phosphine sulphide which may be mentioned is tributylphosphine sulphide.

Examples of phosphine halides which may be mentioned are triphenylphosphine dichloride, triphenylphosphine dibromide, tributylphosphine dichloride and tributylphosphine dibromide, preferably triphenylphosphine dichloride and tributylphosphine dichloride.

Examples of phosphonium salts which may be mentioned are methyltriphenylphosphonium bromide and methyltriphenylphosphonium chloride, tributylphosphonium chloride, tetraethylphosphonium chloride, methyltrioctylphosphonium iodide, allyltriphenylphosphonium chloride and methyltributylphosphonium methosulphate, preferably methyltriphenylphosphonium bromide and methyltriphenylphosphonium chloride.

Examples of halogenophosphines which may be mentioned are diphenylchlorophosphine and phenyldichlorophosphine, preferably phenyldichlorophosphine.

Amongst the said compound categories of organic phosphorus compounds, alkylphosphines and arylphosphines, alkylphosphine oxides and arylphosphine oxides and also the phosphine halides are preferred and the phosphines and phosphine oxides are particularly preferred.

Therefore, the organic phosphorus compounds employed in the process according to the invention are preferably those of the formula

in which
$R^5$, $R^6$ and $R^7$ independently of one another represent alkyl, benzyl, phenyl or chlorine,
Y represents OH, chlorine or bromine,
$R^8$ denotes hydrogen or alkyl or, if X is chlorine or bromine, can also denote chlorine or bromine,
n has the abovementioned meaning,
and in which, furthermore,
$R^8$ and Y together can represent oxygen.

Organic phosphorus compounds particularly preferentially employed in the process according to the invention are those of the formula

in which
$R^9$, $R^{10}$ and $R^{11}$ independently of one another denote alkyl or phenyl,
$R^{12}$ denotes chlorine,
Z denotes chlorine and
n has the abovementioned meaning,
and in which, furthermore,
$R^{12}$ and Z together can represent oxygen.

Of course, mixtures of the organic phosphorus compounds mentioned can also be employed.

Furthermore, it is possible to use compounds from which the indicated organic phosphorus compounds can form under the reaction conditions. For the latter case reference may be made, for example, to the reaction of trisubstituted phosphines with the hydrogen chloride formed during the reaction, to give the corresponding phosphonium salt, and to the reaction of phosphine oxides with phosgene to give phosphine halides and carbon dioxide.

Phenols which can be used for the process according to the invention are, for example, those of the formula

in which
$R^{13}$, $R^{14}$ and $R^{15}$ independently of one another represent hydrogen, alkyl, halogenoalkyl, aralkyl, aryl, halogen, nitro, cyano, alkoxy, alkylthio, aralkoxy, aralkylthio, aryloxy, arylthio, alkylthioalkyl, alkoxyalkyl, halogenoalkylalkoxy, trimethylsilyl, carboxyl, carboalkoxy, formyl, which is optionally in the form of a derivative thereof, alkylamino, which is optionally in the form of a derivative thereof, or alkyl-alkinylamino or dialkylamino, $Ar^1$ denotes the benzene nucleus, the naphthalene nucleus, the anthracene nucleus, the bis-phenylalkylidene system, the diphenyl oxide system, the diphenyl sulphide system, the diphenylsulphone system, the diphenylamine system, a heterocyclic aromatic 5-membered or 6-membered ring or a benzo-fused heterocyclic ring system and m represents a number from 1 to 3, and in which all of the OH groups except one can be in the form of derivatives thereof.

Preferably, phenols of the formula $$R^{16}R^{17}Ar^2(OH)_p \qquad (V)$$

are employed, in which $R^{16}$ and $R^{17}$ represent hydrogen, alkyl, halogenoalkyl, halogen, nitro, cyano or alkoxy, $Ar^2$ denotes the benzene nucleus, the naphthalene nucleus, the quinoline ring system, the benzothiophen ring system, the benzodihydrofuran ring system, the benzodihydropyran ring system, the bisphenyl-alkylidene system or the diphenyl oxide system and p represents the number 1 or 2.

Particularly preferentially, the phenols employed for the process according to the invention are those of the formula $$R^{18}-C_6H_4OH \qquad (VI)$$

in which $R^{18}$ denotes hydrogen, $C_1$-$C_4$-alkyl, $CF_3$, $CCl_3$, Cl, Br, $NO_2$ or $C_1$-$C_4$-alkoxy.

With regard to the range of possible meanings for alkyl, aralkyl and aryl, reference may be made, for example, to the range of meanings already mentioned.

Radicals which may be mentioned as halogenoalkyl are, for example, fluorinated, chlorinated or brominated alkyl radicals with up to 12, preferably up to 6 and particularly preferentially up to 4 carbon atoms, such as trifluoromethyl, trichloromethyl, tribromomethyl and the fluorinated, chlorinated or brominated ethyl, propyl, butyl, hexyl, decyl or dodecyl radicals containing various numbers of fluorine, chlorine or bromine substituents.

Halogen substituents which may be mentioned for the phenols which can be employed according to the invention are, in addition to chlorine and bromine, also fluorine and iodine, preferably fluorine, chlorine or bromine and particularly preferentially chlorine or bromine.

Radicals which may be mentioned as alkoxy are, for example, radicals of aliphatic alcohols with up to 12, preferably up to 6 and particularly preferentially up to 4 carbon atoms, such as methoxy, ethoxy, propoxy, butoxy, hexyloxy, decyloxy or dodecyloxy.

Radicals which may be mentioned as alkylthio are, for example, the thio analogues of the alkoxy radicals mentioned.

Radicals which may be mentioned as aralkoxy are radicals of araliphatic alcohols, such as benzyloxy, phenyl-ethoxy, naphthyl-methoxy and naphthyl-ethoxy, preferably benzyloxy.

Radicals which may be mentioned as aralkylthio are, for example, the thio analogues of the aralkoxy radicals mentioned.

Radicals which may be mentioned as aryloxy are, for example, radicals of phenols, such as phenoxy, naphthyloxy and anthryloxy, preferably phenoxy.

Radicals which may be mentioned as arylthio are, for example, the thio analogues of the aryloxy radicals mentioned.

Radicals which may be mentioned as carboalkoxy are, for example, ester groups with up to 4 carbon atoms, such as carbomethoxy, carboethoxy or carbopropoxy.

If the formyl group is in the form of a derivative, examples which may be mentioned are the 1,3-dioxolan-2-yl or 4,5-dimethyl-1,3-dioxolan-2-yl group.

Examples of dialkylamino which may be mentioned are dimethylamino, diethylamino, dipropylamino, dibutylamino, methylethylamino, methylpropylamino or methylbutylamino. In alkyl-alkinyl-amino groups, alkyl can be the alkyl radicals mentioned and examples of alkinyl which may be mentioned are ethinyl, propinyl or butinyl.

Alkylamino which may be mentioned is amino substituted by only one of the alkyl radicals mentioned. If an amino or alkylamino group is in the form of a derivative, examples which may be mentioned are an amide, such as acetamide, an imine or amidine or a salt thereof with a hydrogen halide or sulphuric acid, or a carbamate group, such as methyl-carbamate or ethyl-carbamate.

If $Ar^1$ represents the bisphenylalkylidene system, an alkylidene group which may be mentioned is a radical with up to 8 carbon atoms, such as the methylene group, the 1,1-ethylidene group, the 1,2-ethylene group, the 2,2-propylidene group, the 1,1,3-trimethyltrimethylene group or the cyclohexylidene group, preferably the methylene group, the 1,1-ethylidene group or the 2,2-propylidene group. Examples which may be mentioned of a heterocyclic aromatic 5-membered or 6-membered ring or of a benzo-fused heterocyclic ring system are pyrrole, furan, thiophen, pyridine, quinoline, isoquinoline, indole, coumarone, thionaphthene, acridine and benzopyran.

m denotes one of the numbers 1, 2 or 3; p denotes 1 or 2.

If $Ar^1$ represents a polynuclear aromatic ring system, the radicals $R^{13}$ to $R^{17}$ and the hydroxyl groups, which are up to 3 in number, can be uniformly or differently distributed between the various nuclei of such a ring system in the formulae (IV) and (V).

The OH groups can all except for one also be in the form of derivatives, for example derivatives obtained by esterification, thus using acetic acid or phosphoric acid, or can be in the form of a mixed alkyl acetal, for example of chloroacetaldehyde, or, in the case of two adjacent OH groups, can be parts of a dioxolane ring.

Examples of individual phenols which can be employed according to the invention are: phenol, o-cresol, m-cresol, p-cresol, xylenols, 4-chlorophenol, hydroquinone, resorcinol, 1-naphthol, 2-naphthol, 1,5-dihydroxynaphthalene, 4,4'-methylene-bis-phenol, 1,1-bis-(4-hydroxyphenyl)-ethane, 2,2-bis-(4-hydroxyphenyl)propane, 4,4'-cyclohexylidene-bisphenol, 4,4'-dihydroxydiphenyl ether, 4,4'-dihydroxydiphenyl sulphone, 4,4'-dihydroxydiphenylsulphone, 2-sec.-butylphenol, 3-sec.-butylphenol, 3,5-di-i-propylphenol, 3,4-dimethylphenol, 3,5-dimethylphenol, 3,5-di-tert.-butylphenol, 3-methylphenol, 3-(2-pentyl)-phenol, 3-(3-pentyl)-phenol, 3,4,5-trimethylphenol, 2-i-propylphenol, 3-i-propylphenol, 3-tert.-butylphenol, 3-methyl-5-i-propyl-phenol, 1-naphthol, 5,6,7,8-tetrahydro-1-naphthol, 3,4-dimethyl-6-chlorophenol, 2-chlorophenol, 3,5-dimethyl-4-dimethylaminophenol, 3,5-dimethyl-4-diallylamino-phenol, 3,5-dimethyl-4-methyl-thiophenol, 2-methyl-4-dimethylamino-phenol, 2-isopropoxy-phenol, 3-aminophenol, amino-phenols in which the $NH_2$ group is protected in the form of the acetate or in the form of an imine or amidine salt or in the form of the methyl-carbamate, 2-(1',3'-dioxolan-2'-yl)-phenol, 2-(4',5'-dimethyl-1',3'-dioxolan-2'-yl)-phenol, 3-methyl-4-dimethylaminophenol, 2-thiobutylphenol, 2-thioethyl-methyl-phenol, 3,5-dimethyl-4-(N,N-dimethylamino)-phenol, 3,5-dimethyl-4-amino-phenol, 2-tert.-butyl-5-methyl-dimethylamino-phenol, 2-(N-methyl-N-propinyl)-aminophenol, 2-allyloxy-phenol, 2-hydroxy-phenol, 2,3-hydroxy-phenol, 3-trimethylsilylphenol and polyhydroxyphenols in which all of the OH groups except one are protected, for example in the form of the acetal of acetone, in the form of a mixed acetal of chloroacetaldehyde or in the form of a mixed ethyl ester of phosphoric acid, and also 1-quinolin-8-ol, 2-methyl-1-quinolin-8-ol, benzothiophen-4-ol, 2,2-dimethyl-7-benzofuranol, 4-chloro-2,3-dihydro-2,2-dimethyl-7-benzofuranol and 3,4-dihydro-2,2-dimethyl-benzopyran-8-ol.

The process according to the invention is illustrated with the aid of the following equation, taking, as an example, the reaction of phenol with phosgene in the presence of an organic phosphorus compound:

The organic phosphorus compound to be employed according to the invention is used in an amount of, for example, 0.1 to 20 mol %, preferably 0.2 to 10 mol % and particularly preferentially 0.5 to 5 mol %, based on each phenol equivalent employed.

Under the action of the additives according to the invention, comprising an organic phosphorus compound, phosgene is used in a molar ratio of 1:1 to 2:1, preferably 1:1 to 1.5:1 and particularly preferentially 1:1 to 1.2:1, based on each phenol equivalent employed. It is possible to use less than the stoichiometric amount of phosgene, but in general this is of no advantage since, in this case, unconverted phenol has to be separated off and the yield falls. The use of larger amounts of phosgene is possible, but brings no further advantages.

The process according to the invention is carried out in a homogeneous liquid phase. The melt of the phenols described, or a solution of the phenols described, can, for example, be regarded as a homogeneous liquid phase. If the reaction is carried out in solution, the solvent employed can be, for example, an aliphatic or aromatic hydrocarbon, such as pentane, hexane, cyclohexane, toluene, xylene or benzene, a halogenated hydrocarbon, such as trichloroethane, chlorobenzene or dichlorobenzene, or an ester, such as ethyl acetate or butyl acetate. Preferably, a halogenated hydrocarbon is employed, and particularly preferentially chlorobenzene is employed.

Preferably, the reaction is carried out without a solvent and only in the melt of the phenol. The space-time yield achieved in this way is higher than that otained when the reaction is carried out in the presence of a solvent. However, it can be advantageous to carry out the reaction in a solvent when the melting point of the phenol to be employed is above the desired reaction temperature and the phenol therefore, at least at the start of the reaction, would react only slowly with the phosgene if the solvent were not present. The presence of a solvent can also be advantageous for controlling and removing the heat of reaction of the exothermic reaction.

The reaction of the process according to the invention is carried out in the temperature range of 60° to 180° C., preferably of 80° to 160° C. and particularly preferentially of 100° to 140° C.

The reaction can be carried out under normal pressure or under elevated pressure. The rise in the partial pressure of phosgene in the reaction mixture under elevated pressure within a closed apparatus increases the rate of reaction. However, due to the formation of hydrogen chloride as the reaction proceeds, the total pressure in a closed apparatus rises sharply and this demands additional expenditure on apparatus and safety measures. In general, therefore, the reaction will be carried out under atmospheric pressure or under only a slightly elevated pressure, for example up to 10 bars, and the hydrogen chloride can be removed discontinuously or continuously from the pressure apparatus.

The process according to the invention can be carried out continuously or discontinuously. A continuous process can be carried out, for example, in a reaction tube, in a stirred kettle cascade, in a loop reactor or in a counter-current column.

To carry out the process according to the invention, the phenol and the intended organic phosphorus compound can, for example, be initially introduced and brought to the desired reaction temperature, with melting. Phosgene is passed in at this temperature, so that only a gentle reflux of phosgene takes place in the reflux condenser fitted on the apparatus. The evolution of hydrogen chloride is then observed using a bubble counter or another suitable device. The reaction has ended when the evolution of hydrogen chloride ceases. The reaction mixture is then separated by distillation into the desired chloroformic acid ester and a residue. This residue contains the organic phosphorus compound. The organic phosphorus compound has not lost its effectiveness for the process according to the invention as a result of this procedure. It can therefore be employed for a further run of the process according to the invention. For this purpose, the bottom product from the distillation of the first reaction run can be worked up, for example by further distillation or by suitable recrystallization, to give the pure organic phosphorus compound, which is then available for a further reaction run. In a further variant of the process according to the invention it is, however, also possible to use the distillation bottom product from the first reaction run, which contains the organic phosphorus compound which is still effective, unchanged in a second reaction run. Because of the simplicity, this latter variant is preferred. It is, however, also possible partly to remove by-products which may have formed and remain in the residue and to recycle only a portion of the residue, with the organic phosphorus compound contained therein, into a subsequent batch. The repeated use of the organic phosphorus compound can be carried out, for example, 2 to 15 times, preferably 2 to 10 times, and particularly preferentially 3 to 6 times. Such repeated use of the organic phosphorus compound is particularly significant when the process according to the invention is carried out continuously. In this case it is then possible, for example, to feed the reaction mixture, which has been removed from the continuously operated reactor and in which the reaction has not necessarily been carried out to complete conversion, into a continuously operated distillation apparatus. In this continuous distillation, the desired chloroformic acid aryl ester is removed as the top product, whilst the bottom product, at least in part, is recycled into the starting mixture for the process according to the invention.

Examples which may be mentioned of chloroformic acid aryl esters which can be prepared by the process according to the invention are: chloroformic acid phenyl ester, chloroformic acid o-cresyl ester, chloroformic acid m-cresyl ester, chloroformic acid p-cresyl ester, chloroformic acid dimethylphenyl ester, chloroformic acid 4-chlorophenyl ester, chloroformic acid naphthyl ester, hydroquinone bis-chloroformate, resorcinol bis-chloroformate, 1,5-dihydroxynaphthalene bis-chloroformate, 4,4'-methylenebisphenyl bis-chloroformate, 1,1-bis-(4-hydroxyphenyl)-ethane bis-chloroformate, 2,2-bis-(4-hydroxyphenyl)-propane bis-chloroformate, 4,4'-cyclohexylidene-bisphenyl bis-chloroformate and 4,4'-dihydroxydiphenyl ether bis-chloroformate.

The chloroformic acid aryl esters, and in particular chloroformic acid phenyl ester, are obtained in high purity by the process according to the invention. They can therefore be further used in the form of the crude products for many purposes. Of course, they can also be further purified in a known manner, for example by distillation or recrystallization.

Chloroformic acid aryl esters are valuable intermediate products, for example in the preparation of dyestuffs, such as Sirius dyestuffs (German Offenlegungsschrift No. 2,325,088 and Ullmanns Enzyklopädie der technischen Chemie (Ullmann's Encyclopaedia of Industrial Chemistry), Volume 4, pages 105, 108 and 109, Urban and Schwarzenberg, 3rd Edition, Berlin-Munich, 1953) and for the preparation of polycarbonate plastics, bactericides and plant protection agents, such as herbicides and insecticides, especially of the category comprising the carbamates, such as are listed, for example, in "The Pesticide Manual (British Crop Protection Council), 6th Edition, 1979" or in K. H. Büchel, "Pflanzenschutz und Schädlingsbekämpfung" ("Plant Protection and Pest Control") (G. Thieme Verlag, 1977, pages 60-72).

Particular mention may be made of the compounds which are listed under the following tradenames and "common names": Sevin (carbaryl), mexacarbate, Methiocarb, Baycarb, Aminocarb (Matacil), propoxur (Baygon), Carbanolate, promecarb, Mobam, Allyxycarb (Hydrol), butacarb, carbofuran, Formetamate hydrochloride, Meobal, Metacrate, bufencarb, Dioxacarb, Macbal, Landrin, CMPO, Isoprocarb, Sapecron, TBPMC, bendiocarb, Ethiofencarb, Hercules 6007 and Promacyl.

Such carbamates can also be obtained by reacting phenols with carbamoyl halides or isocyanates. However, carbamoyl halides are compounds which give cause for concern from the standpoint of work hygiene (see discussion supra). With isocyanates initially only those carbamates which carry a H atom on the carbamate N atom are obtained; the reaction of chloroformates with amines is not subject to this restriction, so that this synthesis route has particular advantages, very particularly for the preparation of carbamates which are disubstituted on the carbamate N atom. The intended uses mentioned are known to those skilled in the art and are described, for example, in (German Auslegeschrift No. 2,131,555, German Auslegeschrift No. 1,213,419 and Ullmann's Enzyklopädie der technischen Chemie (Ullmann's Encyclopaedia of Industrial Chemistry), 4th Edition, Volume 9, page 383, Verlag Chemie 1975.

Compared with the prior art, the process according to the invention offers the following advantages: higher yields and purer products are obtained; there is less corrosion and are also fewer ecological problems and problems with regard to work hygiene; the reaction can also be carried out without applying pressure and the effect of this is higher safety in process control; if the reaction is carried out without additional solvent a higher space-time yield is achieved; the opportunity for repeated use of the organic phosphorus compounds according to the invention lowers the cost of the process.

It is surprising that the organic phosphorus compounds according to the invention effect the reaction of the phenol with the phosgene to give the chloroformic acid aryl ester but do not promote the further condensation to the diaryl carbonate. Surprisingly, the additives according to the invention are superior or at least equivalent to the known additives according to the prior art, in respect of their effect on the reaction, but additionally display the technical advantages indicated.

COMPARISON EXAMPLES

Example 1

(Method according to German Auslegeschrift No. 2,131,555, Example 1)

A mixture of 500 g (5.32 mols) of phenol and 10 to 20 g of dimethylformamide is heated to 100° to 120° C. in a round-bottomed flask which is provided with a stirrer, a gas inlet tube, an internal thermometer and a reflux condenser cooled to −30° to −40° C., with a bubble counter in the gas line. Phosgene is passed in slowly, so that there is—only just—no reflux in the reflux condenser. The contents of the flask become dark in colour.

The reaction is substantially complete when permanent reflux of $COCl_2$ is observed. The reaction mixture is then stirred for a further ½ to 1 hour, or the reflux condenser is removed and further phosgene is passed through the mixture (10 to 20% excess).

Excess phosgene is blown out of the reaction mixture with nitrogen, and chloroformic acid phenyl ester is distilled off in vacuo (boiling point 85° C./20 mm Hg).

761.5 g of a product which is 99.5% pure (according to titration with di-n-butylamine) are obtained (91% of the theoretical yield).

According to analysis by gas chromatography, this product contains about 0.1 to 0.2% of dimethylcarbamoyl chloride.

Example 2

(Method according to Japanese Application No. 23,409/67)

94 g (1 mol) of phenol and 8.3 g of triethyl phosphite are initially introduced into an apparatus as in Example 1 and the mixture is liquefied by melting and allowed to cool to 35° C. The mixture solidifies again on cooling. Phosgene is passed in until reflux takes place. No evolution of HCl is observed in the bubble counter; thus, no substantial reaction takes place.

Example 3

The procedure is as described in Example 2, but the mixture is heated to 120° to 125° C. and about 60 g of $COCl_2$ are introduced in the course of 8 hours.

Excess $COCl_2$ is blown out and 104 g of crude product are obtained; this product solidifies on standing.

The product contains about 15% of chloroformic acid phenyl ester (this corresponds to a yield of 10% of the theoretical yield) and essentially consists of diphenyl carbonate (according to analysis by gas chromatography).

EXAMPLES ACCORDING TO THE INVENTION

Example 4

(a) 500 g (5.32 mols) of phenol and 28 g of triphenylphosphine are initially introduced into an apparatus as described in Example 1, the mixture is warmed to 120° to 125° C. and phosgene is passed in at this temperature. 530 g of $COCl_2$ are consumed within 8 to 10 hours. The reaction mixture is stirred for a further 1 hour at 125° C., the reflux condenser is then replaced by a gas inlet tube and excess $COCl_2$ is blown out with nitrogen.

In contrast to the method according to Examples 1 and 3, the reaction batch is still colourless to pale yellow, even at this stage.

The reaction mixture is distilled in vacuo at 74° to 79° C./12 mm Hg up to an internal temperature of 105° C., and 744 g of chloroformic acid phenyl ester are obtained (purity 99.6% according to titration against amine; yield 89.5% of the theoretical yield).

(b) A further 500 g of phenol are added to the residue, which weighs 100 g, without feeding in fresh triphenylphosphine. The reaction is carried out, as described under 4(a), with 560 g of $COCl_2$. After a phosgenation time of 8 hours, 764 g of distilled 99.7% pure chloroformic acid phenyl ester are obtained (91.5% of the theoretical yield).

(c) The distillation residue is re-used with 500 g of phenol and 540 g of phosgene, without the use of fresh triphenylphosphine. After a phosgenation time of 10 hours, 754 g of distilled chloroformic acid phenyl ester are obtained (purity 99.8%; yield 90.4% of the theoretical yield).

A distillation residue which is of low viscosity, weighs about 200 g and still contains 25% of chloroformic acid phenyl ester remains; the remainder is essentially diphenyl carbamate. The yield after 3 cycles is thus 2,262 g; purity about 99.7% (90.3% of the theoretical yield) in the distillate and, in addition, about 50 g in the residue (2.0% of the theoretical yield).

Example 5

The procedure is as described in Example 4(a), but only 7.0 g of triphenylphosphine are used and 550 g of $COCl_2$ are passed in at about 145° C.

After a reaction time of about 14 hours, distillation yields 640.6 g of 99.6% pure chloroformic acid phenyl ester and 147.2 g of residue, which still contains 28.4% of ester. The total yield is thus 638.0 g (76.6% of the theoretical yield) with, in addition, 41.8 g in the residue (5.0% of the theoretical yield).

Example 6

Phosgene is passed into a batch such as is described in Example 4(a), initially without warming, until sufficient $COCl_2$ is present in the apparatus to boil under reflux. The gas inlet is shut off and the mixture is warmed slowly.

At an internal temperature of from 60° C., escaping HCl gas can be detected at the condenser outlet; this means that the reaction already proceeds at this temperature.

At an internal temperature of from 80° C. the reflux of $COCl_2$ in the condenser also ceases, since the reaction proceeds sufficiently rapidly to consume the available supply of $COCl_2$ within a few minutes.

Example 7

(a) The procedure is as described in Example 4(a), but 30 g of technical grade triphenylphosphine oxide are used in place of triphenylphosphine.

530 g of $COCl_2$ are taken up during a reaction time of 12 hours.

On distillation, 718 g of chloroformic acid phenyl ester are obtained (purity 99.5%; yield 85.7% of the theoretical yield).

(b) The residue, which weighs 110 g, is introduced, without the addition of further triphenylphosphine oxide, into a new batch of 500 g of phenol. 550 g of $COCl_2$ are taken up within 12 hours. The condenser is removed and a further 100 g of $COCl_2$ are passed through the batch. On distillation, 733.1 g of chloroformic acid phenyl ester are obtained (purity 99.2%; yield 87.4% of the theoretical yield). A residue which is of low viscosity when hot, weighs 170 g and still contains 25% of chloroformic acid ester remains. The remainder is essentially diphenyl carbonate.

The total yield is thus 1,442 g (86.6% of the theoretical yield) with, in addition, 42.5 g (5.1% of the theoretical yield) in the residue.

Example 8

The procedure is as in Example 7(a), but the $COCl_2$ is passed in at 110° C.

After a phosgenation time of 13 hours, 530 g of $COCl_2$ had been consumed.

On distillation, 745 g of chloroformic acid phenyl ester are obtained (purity 99.8%; yield 89.3% of the theoretical yield).

A residue remains which weighs 83.5 g and still contains 40% of chloroformic acid phenyl ester (33.4 g; 4.0% of the theoretical yield).

Examples 9–13

Examples with further catalysts, which were carried out in accordance with Example 4(a), are summarised in the Table which follows.

TABLE

| Example | Feed (g of phenol) | Catalyst | Amount | Reaction temperature (°C.) | Phosgene consumption (g) | Reaction time (hours) | Yield in the distillate | (g) in the residue | Yield in the distillate | (% of the theoretical yield) in the residue | total |
|---|---|---|---|---|---|---|---|---|---|---|---|
| 9 | 250 | 1-Phenyl-2,5-dihydro-2-methyl-phosphol oxide | 10.2 g | 120–130 | 300 | 17 | 370.8 | 3.6 | 89.1 | 0.9 | 90.0 |
| 10 | 500 | $C_6H_5$—$PCl_2$ | 34.1 g | 120–125 | 510 | 10 | 604.7 | 64.5 | 72.6 | 7.7 | 80.4 |
| 11 | 500 | $(C_6H_5)_3P(CH_3)Br$ | 39.1 g | 120–125 | 555 | 11 | 713.7 | 40.4 | 85.7 | 4.9 | 90.6 |
| 12 | 500 | $(n-C_4H_9)_3P$ | 21.5 g | 120–125 | 560 | 15 | 729.3 | 43.2 | 87.6 | 5.2 | 92.8 |

| Example | Feed (g of phenol) | Catalyst | Amount | Reaction temperature (°C.) | Phosgene consumption (g) | Reaction time (hours) | Yield in the distillate | (g) Yield in the residue | Yield in the distillate | (% of the theoretical yield) in the residue | total |
|---|---|---|---|---|---|---|---|---|---|---|---|
| 13 | 500 | $(C_6H_5)_3PCl_2$ | 35.5 g | 120–125 | 520 | 8.5 | 774.2 | 26.4 | 93.0 | 3.2 | 96.2 |

EXAMPLE 14

385.7 g (3.0 mols) of p-chlorophenol and 16 g of triphenylphospine are initially introduced into a 1 l flask which is fitted with a stirrer, a gas inlet tube, an internal thermometer and a reflux condenser with intense cooling. The mixture is heated to 125° C. and, in the course of 16 hours, a total of 310 g of $COCl_2$ are passed in so slowly that phosgene just does not start to boil under reflux. After removing the condenser, residual phosgene is driven off with nitrogen and final residues are then removed in vacuo.

Crude chloroformic acid 4-chlorophenyl ester is obtained in a yield, according to titration against amine, of 85% of the theoretical yield, in the form of a pale yellow melt which solidifies on cooling.

Pure ester is obtained by distillation (boiling point 104° C./10 mm Hg).

EXAMPLE 15

324.4 g (3.0 mols) of p-cresol and 15.7 g of triphenylphosphine are initially introduced into an apparatus as described in Example 1, the mixture is heated to 120° to 125° C. and 330 g of $COCl_2$ are introduced in the course of 12 hours. The reaction mixture is stirred for a further 1 hour, excess phosgene is drawn off in vacuo and 461.0 g of chloroformic acid 4-tolyl ester are distilled off; according to titration against di-n-butylamine and according to analysis by gas chromatography this ester is virtually pure (boiling point 92° to 94° C./13 mm Hg). The yield is 90.1%; small amounts are still present in the distillation residue.

EXAMPLE 16

433 g (3.0 mols) of 2-naphthol and 15.7 g of triphenylphosphine are initially introduced into an apparatus as described in Example 1. The mixture is heated to 120° to 125° C. and 325 g of $COCl_2$ are introduced in the course of 12 hours. The reaction mixture is stirred for a further 1 hour, excess phosgene is drawn off in vacuo and crude chloroformic acid 2-naphthyl ester is obtained in a yield of 75% of the theoretical yield.

It can be purified by vacuum distillation (boiling point 136° to 138° C./7.5 mm Hg or 121° to 124° C./1.5 mm Hg).

An adequate result is obtained when 1-naphthol is reacted instead of 2-naphthol.

EXAMPLE 17

125 g of phosgene are passed, in the course of 7 hours, into a solution of 114.0 g (0.5 mol) of 2,2-bis-(4-hydroxyphenyl)-propane ("bisphenol A") and 5.0 g of triphenylphosphine in 1 l of chlorobenzene at 120° to 125° C. at a rate such that $COCl_2$ does not condense or condenses to only a slight extent in a reflux condenser which is connected to the reaction vessel and is cooled with $CO_2$. The reaction mixture is then stirred for 2 hours at 115° C. The solvent is distilled off in a rotary evaporator.

190.7 g of 90.0% pure 2,2-bis-(4-choroformoxyphenyl)-propane are obtained (97.2% of the theoretical yield); (purity determined by titration with di-n-butylamine).

The mass spectrum of a sample recrystallised from naphtha shows signals at m/e=352/354 ("molecular peak") and the NMR spectrum (in $CDCl_3$) shows signals at δ=1.67 (s), 7.1 (d) and 7.3 (d) ppm.

EXAMPLE 18

500 g of 2-sec.-butylphenol (99% pure; =3.30 mols) and 5.8 g of triphenylphosphine are initially introduced into an apparatus as described in Example 1. The mixture is heated to 140°–145° C. and 360 g of phosgene are introduced in the course of 6.5 hours. The reaction mixture is stirred for a further 1 hour and worked up as described in Example 1.

Distillation yields 669.5 g of pure chloroformic acid 2-sec.-butyl-phenyl ester which has a boiling point of 116°–118°/16 mm Hg (literature: 71°/1 mm Hg; (German Offenlegungsschrift No. 2,213,408) and is 100% pure; the purity of the ester can be determined by titration against amine.

This corresponds to a yield of 95.5% of the theoretical yield.

A residue weighing 31 g remains and this still contains the product in an amount making up about 50% of its weight. The catalyst remains in the disillation residue and can be re-used with this in a subsequent reaction batch, without any loss in activity being observed.

What is claimed is:

1. In a process for the preparation of an aromatic chloroformic acid ester by contacting a phenol and phosgene, the improvement wherein the reaction is carried out in a homogeneous liquid phase at a temperature of 60° to 180° C. in the presence of an organic phosphorus compound of the formula $$R^1R^2R^3PR^4{}_nX_n$$

in which $R^1$, $R^2$ and $R^3$ independently of one another represent hydrogen, a straight chain, branched or cyclic alkyl radical of up to 12 carbon atoms, a straight chain, branched or cyclic alkenyl radical of 2 to 12 carbon atoms, an aralkyl radical selected from the group consisting of benzyl, phenylethyl, naphthylmethyl, naphthylethyl and 9-fluorenyl, aryl of up to 15 carbon atoms or halogen and two of the said radicals together with the phosphorus atom can form a 5-membered or 6-membered phosphorus-containing saturated or unsaturated heterocyclic radical of a member selected from the group consisting of a phosphol, a phospholene, a phospholane, a dibenzophospholane and a phosphocyclohexane, X represents OH, homopolar-bonded halogen or an inorganic or organic acid anion, R[4] denotes hydrogen or alkyl of up to 12 carbon atoms or, if X denotes halogen, can also denote halogen and n denotes 0 or 1, and in which, furthermore, R[4] and X together can represent oxygen or sulfur.

2. A process according to claim 1, wherein the organic phosphorus compound is one of the formula $$R^5R^6R^7PR^8_nY_n$$

in which

R[5], R[6] and R[7] independently of one another represent alkyl, benzyl, phenyl or chlorine, Y represents OH, chlorine or bromine, R[8] denotes hydrogen or alkyl or, if Y is chlorine or bromine, can also denote chlorine or bromine, n has the abovementioned meaning, and in which, furthermore, R[8] and Y together can represent oxygen.

3. A process according to claim 1, wherein the organic phosphorus compound is triphenylphosphine, triphenylphosphine oxide, tributylphosphine, tributylphosphine oxide, triphenylphosphine dichloride or tributylphosphine dichloride.

4. A process according to claim 1, wherein the organic phosphorus compound is employed in an amount of 0.1 to 20 mol percent per equivalent of organic hydroxyl group in the phenol.

5. A process according to claim 1, wherein the organic phosphorus compound is re-used several times.

6. A process according to claim 1, wherein the resultant reaction mixture is subjected to distillation and the distillation residue which contains phosphorus compound is employed for a subsequent preparation of an aromatic chloroformic acid ester by reaction of a phenol with phosgene without further working up the distillation residue.

7. A process according to claim 1, wherein the reaction is carried out at a temperature between 80° and 160° C.

8. A process according to claim 1, wherein the reaction is carried out in the presence of an inert solvent.

9. A process according to claim 1, wherein the reaction is carried out in the melt.

10. A process according to claim 1, wherein the phenol employed is one of the formula $$R^{13}R^{14}R^{15}Ar^1(OH)_m$$

in which

R[13], R[14] and R[15] independently of one another represent hydrogen, straight chain, branched or cyclic alkyl of up to 12 carbon atoms, halogenoalkyl where the halogen substituent is chlorine, bromine, fluorine or iodine and the alkyl substituent is a straight chain, branched or cyclic alkyl radical of up to 12 carbon atoms, aralkyl selected from the group consisting of benzyl, phenylethyl, naphthylmethyl, naphthylethyl and 9-fluorenyl, aryl of up to 15 carbon atoms, halogen selected from the group consisting of fluorine, chlorine, bromine and iodine, nitro, cyano, alkoxy where the alkyl group has up to 12 carbon atoms, alkylthio where the alkyl group has up to 12 carbon atoms, aralkoxy selected from the group consisting of benzyloxy, phenylethoxy, naphthylmethoxy and naphthylethoxy and the thioanalogs thereof, aryloxy selected from the group consisting of phenoxy, naphthoxy and anthryloxy and the thioanalogs thereof, alkylthioalkyl where each alkyl group is a straight chain, branched or cyclic alkyl having up to 12 carbon atoms, alkoxyalkyl where each alkyl group is a straight chain, branched or cyclic alkyl radical of up to 12 carbon atoms, halogenoalkylalkoxy where each alkyl group is a straight chain, branched or cyclic alkyl radical of up to 12 carbon atoms, trimethylsilyl, carboxyl, carboalkoxy where the alkyl group of the alkoxy radical is a straight chain, branched or cyclic alkyl radical of up to 12 carbon atoms, formly, alkylamino where the alkyl group is a straight chain, branched or cyclic alkyl radical of up to 12 carbon atoms, or alkylalkinylamino where the alkyl group is a branched, straight chain or cyclic alkyl radical of up to 12 carbon atoms or dialkylamino where each alkyl group is a straight chain, branched or cyclic alkyl radical of up to 12 carbon atoms, Ar[1] denotes the benzene nucleus, the naphthalene nucleus, the anthracene nucleus, the bis-phenylalkylidene system, the diphenyl oxide system, the diphenyl sulphide system the diphenylsulphone system, the diphenylamine system, a heterocyclic aromatic 5-membered or 6-membered ring or a benzo-fused heterocyclic ring system and m represents a number from 1 to 3, and in which all of the OH groups except one can be in the form of derivatives thereof.

* * * * *